US010692607B2

(12) United States Patent
Viswanath et al.

(10) Patent No.: US 10,692,607 B2
(45) Date of Patent: Jun. 23, 2020

(54) TREATMENT PLANNING AND EVALUATION FOR RECTAL CANCER VIA IMAGE ANALYTICS

(71) Applicant: Case Western Reserve University, Cleveland, OH (US)

(72) Inventors: Satish Viswanath, Cleveland, OH (US); Anant Madabhushi, Beachwood, OH (US); Jacob Antunes, Cincinnati, OH (US)

(73) Assignee: Case Western Reserve University, Cleveland, OH (US)

( * ) Notice: Subject to any disclaimer, the term of this patent is extended or adjusted under 35 U.S.C. 154(b) by 1116 days.

(21) Appl. No.: 15/076,114

(22) Filed: Mar. 21, 2016

(65) Prior Publication Data
US 2017/0053090 A1 Feb. 23, 2017

Related U.S. Application Data

(60) Provisional application No. 62/206,638, filed on Aug. 18, 2015.

(51) Int. Cl.
*G16H 50/50* (2018.01)
*A61B 5/055* (2006.01)
(Continued)

(52) U.S. Cl.
CPC ............. *G16H 50/50* (2018.01); *A61B 5/055* (2013.01); *A61B 34/10* (2016.02);
(Continued)

(58) Field of Classification Search
CPC .... A61B 34/10; A61B 5/055; G06K 2209/05; G06K 9/4619; G06K 9/6212;
(Continued)

(56) References Cited

U.S. PATENT DOCUMENTS 9,811,904 B2 * 11/2017 Lambin ................ G06T 7/0012
2014/0140594 A1 * 5/2014 Mahadevan-Jansen ......................
G06T 7/0012
382/128
(Continued)

OTHER PUBLICATIONS

Brown et al. "Prepoperative assessment of prognostic factors in rectal cancer using high-resolution magnetic resonance imaging." British Journal of Surgery 90: 355-364. 2003.*
(Continued)

*Primary Examiner* — Amanda Lauritzen Moher
(74) *Attorney, Agent, or Firm* — Eschweiler & Potashnik, LLC

(57) ABSTRACT

Methods and apparatus associated with predicting colorectal cancer tumor invasiveness are described. One example apparatus includes a set of circuits, and a data store that stores radiological images of tissue demonstrating colorectal cancer. The set of circuits includes a circumferential resection margin (CRM) prediction circuit that generates a CRM probability score for a diagnostic radiological image, an image acquisition circuit that acquires a diagnostic radiological image of a region of tissue demonstrating colorectal cancer pathology and that provides the diagnostic radiological image to the CRM prediction circuit, and a training circuit that trains the CRM prediction circuit to quantify chemoradiation response in the region of tissue represented in the diagnostic radiological image. The training circuit trains the CRM prediction circuit using a set of composite images.

17 Claims, 6 Drawing Sheets

(51) Int. Cl.
| | |
|---|---|
| *G06K 9/62* | (2006.01) |
| *A61B 34/10* | (2016.01) |
| *G06T 7/00* | (2017.01) |
| *G06K 9/46* | (2006.01) |
| *G06N 20/00* | (2019.01) |
| *G06N 5/00* | (2006.01) |
| *G06N 3/08* | (2006.01) |
| *G01R 33/56* | (2006.01) |

(52) U.S. Cl.
CPC ....... *G01R 33/5608* (2013.01); *G06K 9/4619* (2013.01); *G06K 9/6212* (2013.01); *G06K 9/6247* (2013.01); *G06K 9/6269* (2013.01); *G06N 3/08* (2013.01); *G06N 5/00* (2013.01); *G06N 20/00* (2019.01); *G06T 7/0012* (2013.01); *G06K 2209/05* (2013.01); *G06T 2207/10088* (2013.01); *G06T 2207/20064* (2013.01); *G06T 2207/20081* (2013.01); *G06T 2207/30028* (2013.01); *G06T 2207/30096* (2013.01)

(58) Field of Classification Search
CPC ................ G06K 9/6247; G06K 9/6269; G06T 2207/10088; G06T 2207/20064; G06T 2207/20081; G06T 2207/30028; G06T 2207/30096; G06T 7/0012; G16H 50/50; G01R 33/5608; G06N 3/08; G06N 5/00; G06N 20/00
See application file for complete search history.

(56) References Cited

U.S. PATENT DOCUMENTS

| | | | | |
|---|---|---|---|---|
| 2015/0289795 | A1* | 10/2015 | Batlle Gomez | ...... C12Q 1/6886 514/314 |
| 2015/0356730 | A1* | 12/2015 | Grove | .................. G01N 23/046 382/124 |
| 2017/0071496 | A1* | 3/2017 | Gillies | ............... G01R 33/5602 |

OTHER PUBLICATIONS

Barbaro et al. "Locally advanced rectal cancer: MR imgining in prediction of response after preoperative chemotherapy and radiation therapy." Radiology 250(3): 730-739. 2009.*

Smith et al. "Prognostic significance of magnetic resonance imaging-detected extramural vascular invasion in rectal cancer." British Journal of Surgery 95: 229-236. 2008.*

Marije P. van der Paardt et al. "Patients who undergo preoperative chemoradiotherapy for locally advanced rectal cancer restaged by using diagnostic MR imaging: A systematic review and meta-analysis." Radiology 269(1): 101-112. 2013.*

Jeonghyun Kang et al. "Circumferential resection margin involvement in stage III rectal cancer patients treated with curative resection followed by chemoradiotherapy: A surrogate marker for local recurrence?" Yonsei Med J 54(1): 131-138. 2013.*

Ueno, et al. "Histological Categorisation of Fibrotic Cancer Stroma in Advanced Rectal Cancer." Gut 2004;53:581-586, published in 2004.

* cited by examiner

TREATMENT PLANNING AND EVALUATION FOR RECTAL CANCER VIA IMAGE ANALYTICS

CROSS REFERENCE TO RELATED APPLICATIONS

This application claims the benefit of U.S. Provisional Application 62/206,638 filed Aug. 18, 2015.

BACKGROUND

Tens of thousands of patients are diagnosed with colorectal cancer each year. Approximately twenty percent of those patients will experience locally recurrent tumors. Conventional clinical standard-of-care involves adjuvant chemoradiation therapy to reduce tumor burden, followed by pre-operative treatment planning with manual inspection of pre-surgical magnetic resonance imaging (MRI) imagery. Pre-operative planning in colorectal cancer is highly dependent on the extent of tumor invasion into the mesorectum and perirectal fat. However, the measure of tumor distance to the mesorectal wall, defined as the circumferential resection margin (CRM), is only measured after surgery in conventional approaches. Conventional approaches thus delay adjuvant intervention that could improve patient outcomes.

Conventional approaches to colorectal treatment planning involve manual inspection of pre-operative MRI imagery. However, conventional approaches lack definitively identified imaging characteristics of treatment response, which leads to sub-optimal surgical planning as well as misdiagnosis of complete or incomplete treatment response. Thus, almost all colorectal patients subject to conventional approaches undergo some form of colorectal excision surgery, regardless of the stage of the cancer or the effectiveness of treatment. In the United States alone, up to 8,000, or twenty percent of colorectal patients are subjected to morbid total mesorectal excision, despite demonstrating pathologic complete response to pre-surgical neoadjuvent chemotherapy.

Conventional approaches to colorectal treatment planning may involve expert evaluation of pre-surgical restaging MRI. Expert evaluation of pre-surgical restaging MRI is qualitative and has no standardized reporting system. Expert evaluation of pre-surgical restaging MRI is thus also prone to inter-operator variability. Furthermore, identifying the extent of tumor invasion using pre-surgical restaging MRI is subjective and depends on the individual expert's skill at accurately identifying the extent of tumor invasion versus confounding treatment effects in vivo.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
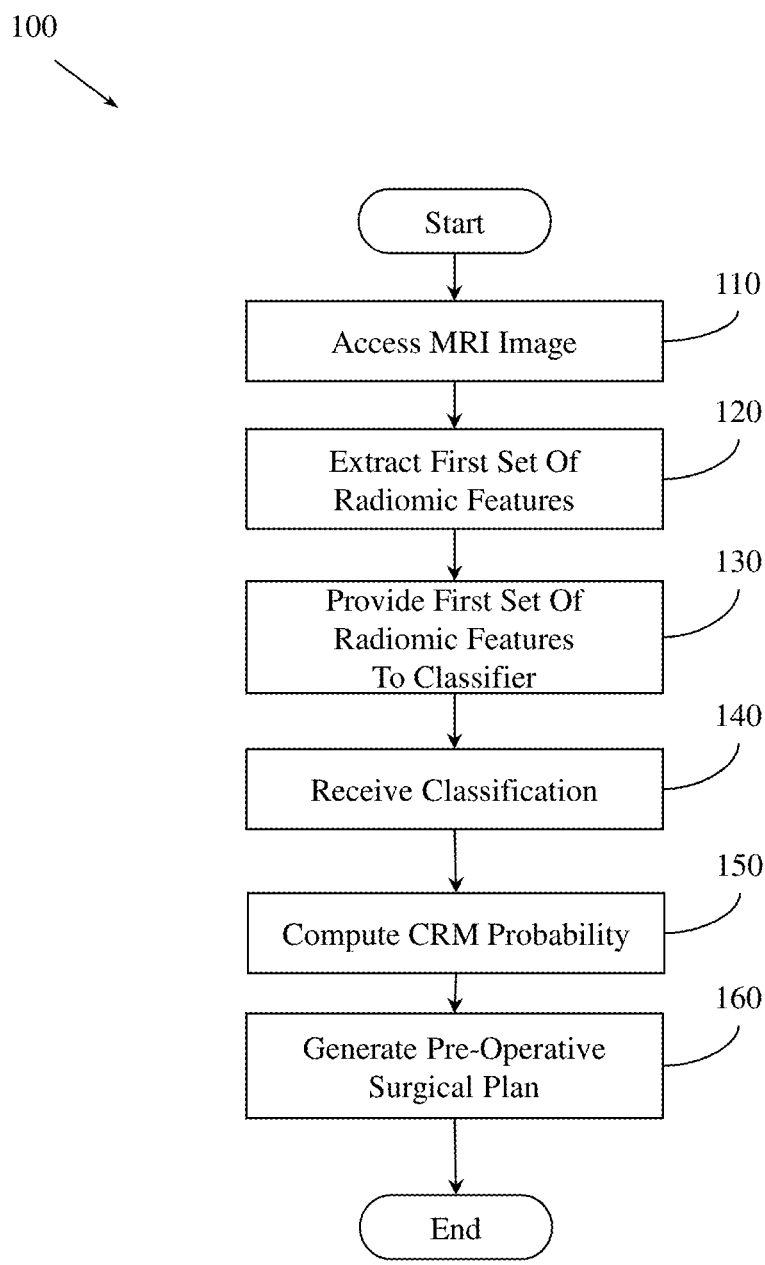
FIG. 1 illustrates an example method for predicting colorectal cancer tumor invasiveness.

Example methods and apparatus identify radiomic features predictive of tumor invasiveness on a restaging MRI image of a region of tissue demonstrating colorectal cancer. Example methods and apparatus identify quantitative differences between different treatment pathologies and confounding treatment effects on in vivo rectal MRI. By more accurately identifying the presence or absence of residual disease, example methods and apparatus improve surgical margin planning by facilitating the minimization of unneeded tissue excision. Example methods and apparatus more accurately identify patients who may not need aggressive surgery and who may instead undergo intensive follow-up treatment, based on the identification of complete or incomplete response to adjuvant chemoradiation.

In one embodiment, a set of MRI images is generated prior to surgery by imaging a population of colorectal cancer patients using an axial T2 weight (T2w) turbo-spin echo MRI sequence post-neoadjuvant chemotherapy. In this embodiment, at least 78 first order statistical features, gray level features, gradient features, Haralick features, and multi-scale oriented Gabor radiomic feature maps are extracted from the set of MRI images. The at least 78 features are extracted from T2w volumes on a per-voxel basis. The extracted features capture structural homogeneity and structural heterogeneity characteristics within the region of tissue imaged. Members of the set of MRI images are annotated, either automatically or by an expert human pathologist. Members of the set of MRI images are annotated for residual colorectal cancer, chemoradiation treatment effects including fibrosis or mucosal ulceration, and normal tissue. Other anatomic structures or landmarks may also be annotated.

Example methods and apparatus identify radiomic features in the set of MRI images by correlating feature statistics, including median, variance, kurtosis, and skewness, with the ratio of carcinoembryonic antigen (CEA) levels measured pre-treatment and CEA levels measured post treatment. Example methods and apparatus calculate an optimal combination of the identified features by performing a principal component analysis (PCA) of the identified features. An optimal combination of the identified features is a combination that discriminates with at least 90% accuracy between patients who were identified following surgical resection as having positive CRM or negative CRM. Tissue is classified as CRM positive when tumor tissue is within 1 mm of the mesorectal wall. Tissue is classified as CRM negative when tumor tissue is localized to the mesorectum. Example methods and apparatus employ a heat map of Gabor features to differentiate between positive CRM and negative CRM. T2w intensity between positive CRM tissue and negative CRM tissue may not be visible to the naked human eye. However, Gabor features express differentially between positive CRM tissue and negative CRM tissue by capturing multi-scale gradient information that is associated with tumor invasiveness.

Example apparatus and methods use histologic slices and deformable co-registration to map different pathological annotations onto imaging. In one embodiment, a histological slice is combined with in vivo, pre-surgical MRI imagery using elastic registration techniques. MRI imagery and histology slices of resected colorectal tissue with CRM positive or CRM negative invasion are examined. Following high-resolution scanning of histology slides of colorectal tissue, structural components are annotated automatically or by an expert pathologist. Residual tumor, benign treatment effects of ulceration or fibrosis, and normal tissue including mucosal layers, muscle, or fat, may be annotated. The annotations may be mapped onto MRI images of the region of tissue through co-registration of the histology with MRI images. At least thirteen textural features are extracted from the MRI images, from which a quantitative descriptor map that captures sub-visual differences in tissue intensity is generated. Regions of tissue demonstrating residual disease or treatment effects may be differentiated by measuring difference entropy in the MRI images. Differences in tumor microenvironment are captured by difference entropy, which quantifies the entropy or chaos intensity differences between small neighborhoods within an MRI image.

In one embodiment, MRI-derived radiomic features are extracted to identify and distinguish CRM positive tissue from CRM negative tissue. MRI-derived features may include intensity statistics, Haralick features, Gabor features, or other textural features that facilitate characterizing the textural appearance of the region of tissue and identifying those features that distinguish CRM positive from CRM negative tissue. The textural features may be extracted based on intensity alone without considering shape, or the textural features may be extracted with consideration of shape. In another embodiment, shape features may also be extracted and used to distinguish CRM positive from CRM negative tissue.

Example methods and apparatus may train a classifier to detect computer extracted textural or shape features associated with colorectal cancer tumor invasion in a radiological image. Machine learning techniques may be used to train a classifier to differentiate CRM positive tissue from CRM negative tissue using the combined histology-MRI data. The classifier may distinguish tissue likely to be CRM positive from tissue likely to be CRM negative by identifying texture or shape features associated with colorectal cancer in the MRI imagery. Example methods and apparatus may train the classifier using support vector machine (SVM) regression or other machine learning techniques.

Example methods and apparatus may also train a classifier to classify a response to a treatment demonstrated by a region of tissue. Tissue in a region of interest represented in MRI data, in a composite MRI image, or in combined histology-MRI data may demonstrate a response to a treatment. The treatment may include chemoradiation treatment. A response to a treatment may be classified according to a pathological stage, a pathological tumor regression grade, a pathological tumor type, or a pathological tumor differentiation level represented in the MRI image. The classifier may distinguish tissue likely to belong to a first class of response to treatment from tissue likely to belong to a second, different class of response to treatment by identifying texture or shape features associated with a particular class of response to treatment. Example methods and apparatus may extract a third set of radiomic features from the set of MRI images, and generate a third set of radiomic feature statistics from the third set of radiomic features. The third set of radiomic feature statistics may include a textural feature, a gray level feature, a gradient feature, a Haralick feature, a difference entropy statistic, or a multi-scale oriented Gabor feature map. Example methods and apparatus may identify a second subset of radiomic features by identifying a subset of the third set of radiomic feature statistics that identifies a response to a treatment demonstrated by the region of tissue. In one embodiment, an optimal combination of the identified features is a combination that distinguishes a class of response to treatment with at least 90% accuracy. Regions of tissue demonstrating different classes of response to treatment may be differentiated by measuring difference entropy in the MRI images.

Machine learning techniques may be used to train the classifier to differentiate tissue more likely to experience five year local recurrence from tissue less likely to experience five year local recurrence based, at least in part, on the class of response. For example, a region of tissue demonstrating a class of response associated with a first pathological tumor regression grade may be more likely to experience five year local recurrence than a region of tissue demonstrating a class of response associated with a second pathological tumor regression grade. The classifier may be trained on a set of MRI images or composite MRI images. The set of composite images may be generated by registering a pre-chemoradiation MRI image with a post-chemoradiation MRI image. The pre-chemoradiation MRI image may be a pre-neoadjuvant chemoradiation image. The post-chemoradiation MRI image may be a post-neo-adjuvant chemoradiation image. The pre-chemoradiation MRI image may be registered with the post-chemoradiation MRI image using affine co-registration and deformable co-registration, or by using other registration techniques.

By fusing histology with MRI and image analytics to train classifiers to distinguish CRM positive from CRM negative tissue, or to classify a response to treatment demonstrated by tissue in a region of interest, example methods and apparatus facilitate more accurate detection of invasive colorectal cancer on pre-operative MRI imagery. Example methods and apparatus thus produce the concrete, real-world technical effect of increasing the accuracy with which response to treatment may be assessed, and with which further treatment, including surgery, may be planned. Additionally, example apparatus and methods increase the probability that at-risk patients receive timely treatment tailored to the particular pathology they exhibit. Example methods and apparatus may also reduce the number of invasive procedures needed to accurately predict response to treatment in colorectal cancer patients. The additional technical effect of reducing the expenditure of resources and time on patients who are less likely to experience disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example method 100 for predicting colorectal cancer tumor invasiveness. Method 100 includes, at 110, accessing a magnetic resonance imaging (MRI) image of a region of tissue demonstrating colorectal cancer pathology. The MRI image may be a restaging MRI image of a region of tissue in a patient experiencing a recurrence of disease after treatment. Accessing the MRI image may include accessing an MRI image of a region of colorectal tissue. The MRI image may include a texture feature or a shape feature. The MRI image may be stored, for example, in a computer memory or may be provided across a computer network. In one embodiment, the MRI image is a 3 Tesla (T) T2 weighted (T2w) MRI image. In another embodiment, different imaging techniques may be employed. In different embodiments, image sizes, in-plane resolutions, or distances between MRI images may be user adjustable.

Method 100 also includes, at 120, extracting a first set of radiomic features from the MRI image. The first set of radiomic features may be extracted using, for example, a statistical approach, including edge detection or co-occurrence matrix approaches. Region-based or boundary-based approaches may also be used. Examples of feature extraction approaches include discrete wavelet transform (DWT) approaches or projection onto convex sets (POCS) approaches. Automated computer vision or pattern recognition techniques may be employed to extract the first set of radiomic features. The set of radiomic features includes intensity statistics, Haralick features, Gabor features, or other textural features used to characterize the textural appearance of colorectal tissue represented in the MRI image. For example, the set of radiomic feature statistics may include a textural feature, a gray level feature, a gradient feature, a Haralick feature, a difference entropy statistic, or a multi-scale oriented Gabor feature map. A member of the set of radiomic features may be a first order statistic. In one embodiment, a member of the set of radiomic feature statistics is extracted from a T2w volume on a per-voxel basis. The set of radiomic features may be used to identify features that distinguish positive CRM tissue from negative CRM tissue. In another embodiment, shape features may be extracted from the MRI image and used to distinguish positive CRM tissue from negative CRM tissue.

Method 100 also includes, at 130, providing the MRI image or the first set of radiomic features to an automated colorectal cancer classifier. The MRI image or the first set of radiomic features may be stored, for example, in a computer memory, or may be provided across a computer network.

Method 100 also includes, at 140 receiving a classification of the region of tissue from the automated colorectal cancer classifier. The automated colorectal cancer classifier may classify the region of tissue as CRM positive or CRM negative. In one embodiment, the automated colorectal cancer classifier is trained on a set of composite images. A composite image is formed by registering a digitized H&E stained excised colorectal specimen slice with a pre-surgery, in vivo MRI image. Quantitative fusion of the pathology slice and the MRI image is performed using thin-plate spline-based elastic registration that warps matched landmarks and gross anatomy into spatial alignment. In another embodiment, other types of registration may be used.

Method 100 also includes, at 150, computing a probability that the region of tissue is CRM positive or CRM negative. Method 150 computes the probability based, at least in part, on the first set of radiomic features and the classification. In one embodiment, method 100 computes the probability that the region of tissue is CRM positive or CRM negative with at least a 90 percent accuracy rate.

Method 100 also includes, at 160, generating a pre-operative surgical plan based, at least in part, on the probability. Method 100 may control an automated ablation device using the pre-operative surgical plan based, at least in part, on the probability and the MRI image. Developing a pre-operative surgical plan based on more accurate prediction of a patient's CRM class may result in fewer unneeded, invasive procedures being performed. Avoiding unnecessary total mesorectal excision may have a measurable, quantifiable increase in colorectal cancer treatment success rates.

Example methods and apparatus facilitate applying a more appropriately determined treatment based on the pre-operative surgical plan associated with the area of tissue under investigation. Using a more appropriately determined and applied treatment may lead to less therapeutics being required for a patient or may lead to avoiding or delaying a biopsy, a resection, or other invasive procedure. When regions of cancerous tissue are more quickly and more accurately classified as likely or unlikely to be CRM positive, or likely or unlikely to experience five year recurrence, patients with poorer prognoses may receive a higher proportion of scarce resources (e.g., therapeutics, physician time and attention, hospital beds). Patients with better prognoses may thus be spared unnecessary treatment and potential side-effects, which in turn spares unnecessary expenditures and resource consumption. Example methods and apparatus therefore have the real-world, quantifiable effects of improving patient outcomes and reducing resource expenditure.

While FIG. 1 illustrates various actions occurring in serial, it is to be appreciated that various actions illustrated in FIG. 1 could occur substantially in parallel. By way of illustration, a first process could access an MRI image of a region of tissue demonstrating cancerous pathology, a second process could extract radiomic features from the MRI image, and a third process could compute a probability that the region of tissue is CRM positive or CRM negative. While three processes are described, it is to be appreciated that a greater or lesser number of processes could be employed and that lightweight processes, regular processes, threads, and other approaches could be employed.

Figure 2:
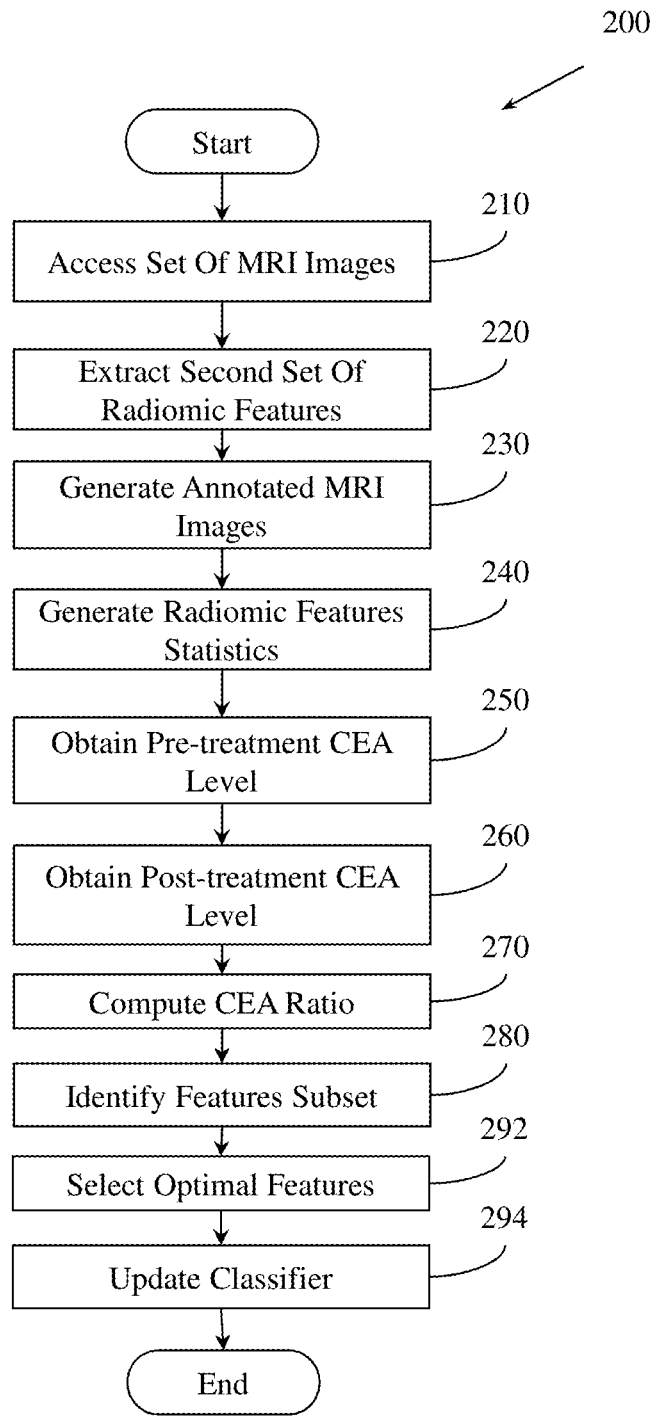
FIG. 2 illustrates an example method for training an automated colorectal cancer classifier.

FIG. 2 illustrates a method 200 for training a colorectal cancer classifier to distinguish CRM positive tissue from CRM negative tissue. Method 200 may be performed independently of method 100 or may be performed as an additional action during the performance of method 100. Method 200 includes, at 210, accessing a set of MRI images of a region of tissue demonstrating colorectal cancer pathology. The set of MRI images may be provided directly from an MRI apparatus, or indirectly via an electronic database, a memory, a network, or other electronic communication channel. A member of the set of MRI images includes a radiomic feature. A radiomic feature may be a texture feature or a shape feature. In one embodiment, a member of the set of MRI images is a 3T axial T2w turbo-spin echo MRI image. In another embodiment, a member of the set of MRI images may be a CT image.

Method 200 also includes, at 220, extracting a second set of radiomic features from the set of MRI images. In one embodiment, example methods and apparatus may extract at least 78 radiomic features from the set of MRI images. The second set of radiomic features may include a textural feature, a gray level feature, a gradient feature, a Haralick feature, a difference entropy statistic, or a multi-scale oriented Gabor feature map. In another embodiment, a different number of radiomic features, or other, different radiomic features may be extracted. The second set of radiomic features may be extracted using computer vision or pattern recognition approaches. The second set of radiomic features may also be extracted using for example, a statistical approach, including edge detection or co-occurrence matrix approaches. Region-based or boundary based approaches may also be used. In another embodiment, other numbers of sets of radiomic features may be extracted from the set of MRI images. For example, a third set of radiomic features may be extracted from the set of MRI images.

Method 200 also includes, at 230, generating an annotated set of MRI images from the set of MRI images. The annotated set of MRI images may be generated by automatically annotating the set of MRI images, or the set of MRI images may be annotated by an expert pathologist. A member of the annotated set of MRI images may include annotations of landmarks, gross anatomy, or other structures.

Method 200 also includes, at 240, generating a set of radiomic feature statistics from the second set of radiomic features. The set of radiomic feature statistics includes median, variance, kurtosis, or skewness statistics associated with the second set of radiomic features. In another embodiment, the set of radiomic feature statistics may include other, different statistics. The set of radiomic feature statistics may be stored in a register, in computer memory, on a hard disk, in a solid state device (SSD), or on other external electronic data storage devices. In another embodiment, example methods and apparatus may generate a second set of radiomic feature statistics from a third set of radiomic features.

Method 200 also includes, at 250, obtaining a pre-treatment carcinoembryonic antigen (CEA) level for the region of tissue. Method 200 also includes, at 260, obtaining the post-treatment CEA level for the region of tissue. Obtaining the pre-treatment CEA level or the post-treatment CEA level may include determining the pre-treatment CEA level or the post-treatment CEA level. Pre-treatment CEA and post-treatment CEA levels may be determined using a CEA blood serum test. Obtaining a pre-treatment CEA level or a post-treatment CEA level may also include receiving the pre-treatment CEA level or the post-treatment CEA level via an electronic database, a memory, a network, or other electronic communication channel. Obtaining a pre-treatment CEA level or a post-treatment CEA level may also include acquiring the pre-treatment CEA level or the post-treatment CEA level from a computer memory or from a computer-readable storage medium or computer-readable storage device. Method 200 also includes, at 270, computing a CEA ratio based on the pre-treatment CEA level and the post-treatment CEA level.

Method 200 also includes, at 280, identifying a subset of radiomic features by correlating the second set of radiomic feature statistics with the CEA ratio. For example, radiomic feature statistics, including median, variance, kurtosis, or skewness, may be correlated with the ratio of CEA levels measured pre-treatment and measured post-treatment. Correlating the second set of radiomic feature statistics with the CEA ratio facilitates identifying those radiomic features that most accurately distinguish CRM positive tissue from CRM negative tissue. Method 200 may quantify differences in intensity distribution between CRM positive tissue and CRM negative tissue across different radiomic features to select better performing radiomic features to include in the subset of radiomic features. For example, a Gabor wavelet with xy=0, bandwidth=1, and wavelength=22.6 voxels may express differences between CRM positive and CRM negative tissue more accurately than a Gabor wavelet with xy=1.964, bandwidth=1, and wavelength=8.2 voxels.

Method 200 also includes, at 292, selecting an optimal combination of radiomic features from the subset of radiomic features. Selecting an optimal combination of radiomic features may include performing a principal component analysis (PCA) on the subset of radiomic features. In one embodiment, the optimal combination includes at least ten features, at least one of which is a Gabor feature. In another embodiment, other numbers or types of features may be included in the optimal combination. An optimal combination of radiomic features is a combination of radiomic features that most accurately distinguishes CRM positive tissue from CRM negative tissue based on the available set of radiomic features and the set of MRI images. In one embodiment, selecting an optimal combination of radiomic features may include performing a logistic regression on the subset of radiomic features. In another embodiment, example methods and apparatus may select a second optimal combination of radiomic features. A second optimal combination of radiomic features is a combination of radiomic features that most accurately distinguishes a first class of response to a treatment from a second, different class of response to a treatment, based on the available set of radiomic features and the set of MRI images.

Method 200 also includes, at 294, updating the colorectal cancer classifier using the optimal combination of radiomic features and the annotated set of MRI images. Updating the colorectal cancer classifier may include training the colorectal cancer classifier using a set of composite images. A member of the set of composite images is generated by registering a pre-surgical MRI image of a region of tissue demonstrating colorectal cancer with an annotated ex-vivo, post-surgical rectal pathology image of the region of tissue. The pre-surgical MRI image may be registered with the annotated ex-vivo, post-surgical rectal pathology image using thin-plate control-point spline based elastic registration. In another embodiment, other registration approaches may be used, including affine registration. In one embodiment, the colorectal cancer classifier is an automated colorectal cancer classifier. Example methods and apparatus may update a first automated colorectal cancer classifier using the optimal combination of radiomic features and the annotated set of MRI images, or update a second, different colorectal cancer classifier using a second optimal combination of radiomic features and the annotated set of MRI images. In another embodiment, the first or second automated colorectal cancer classifier may be updated using the optimal combination of radiomic features, the second optimal combination of radiomic features, and the annotated set of MRI images.

The set of annotated ex-vivo, post-surgical rectal pathology images is generated by annotating post-surgical pathology slides to indicate residual colorectal cancer, chemoradiation treatment effects, and normal tissue. Chemoradiation effects may include fibrosis or mucosal ulceration. Normal tissue may include muscle, fat, or mucosal layers. In another embodiment, other features or structures may be annotated in the annotated ex-vivo, post-surgical rectal pathology image. In one embodiment, an annotated ex-vivo, post-surgical rectal pathology image is an H&E stained image. In another embodiment, other types of stain, scanning magnification, or pixel sizes may be employed.

In one embodiment, the classifier may be trained to distinguish CRM positive from CRM negative tissue, based, at least in part, on the set of composite images, a texture feature, or a shape feature. Training a classifier may include training an SVM using the set of composite images as a set of training examples. The SVM may be trained to classify a region of tissue based on radiomic features associated with CRM positive or CRM negative tissue. Example methods and apparatus may extract features from the composite radiological-pathological data and apply SVM regression to characterize the level of invasion. Example methods and apparatus may extract features from the composite radiological-pathological data using computer-vision approaches or a pattern analysis device. In one embodiment, SVM regression may be used to determine a CRM score. For example, the SVM may learn to classify an image based on a texture feature that was extracted from the radiological image that matches a previously learned texture feature to within a threshold level of accuracy. The threshold level of accuracy may be user adjustable. Other machine learning approaches may also be employed, including clustering, decision trees, or artificial neural networks. In another embodiment, the classifier may be trained to distinguish a response to a treatment demonstrated in a region of tissue. The response to a treatment may be classified according to a pathological stage, a pathological tumor regression grade, a pathological tumor type, or a pathological tumor differentiation level. For example, the SVM may learn to classify an image according to a pathological stage, a pathological tumor regression grade, a pathological tumor type, or a pathological tumor differentiation level based on a feature extracted from the radiological image that matches a previously learned texture feature to within a threshold level of accuracy.

Figure 3:
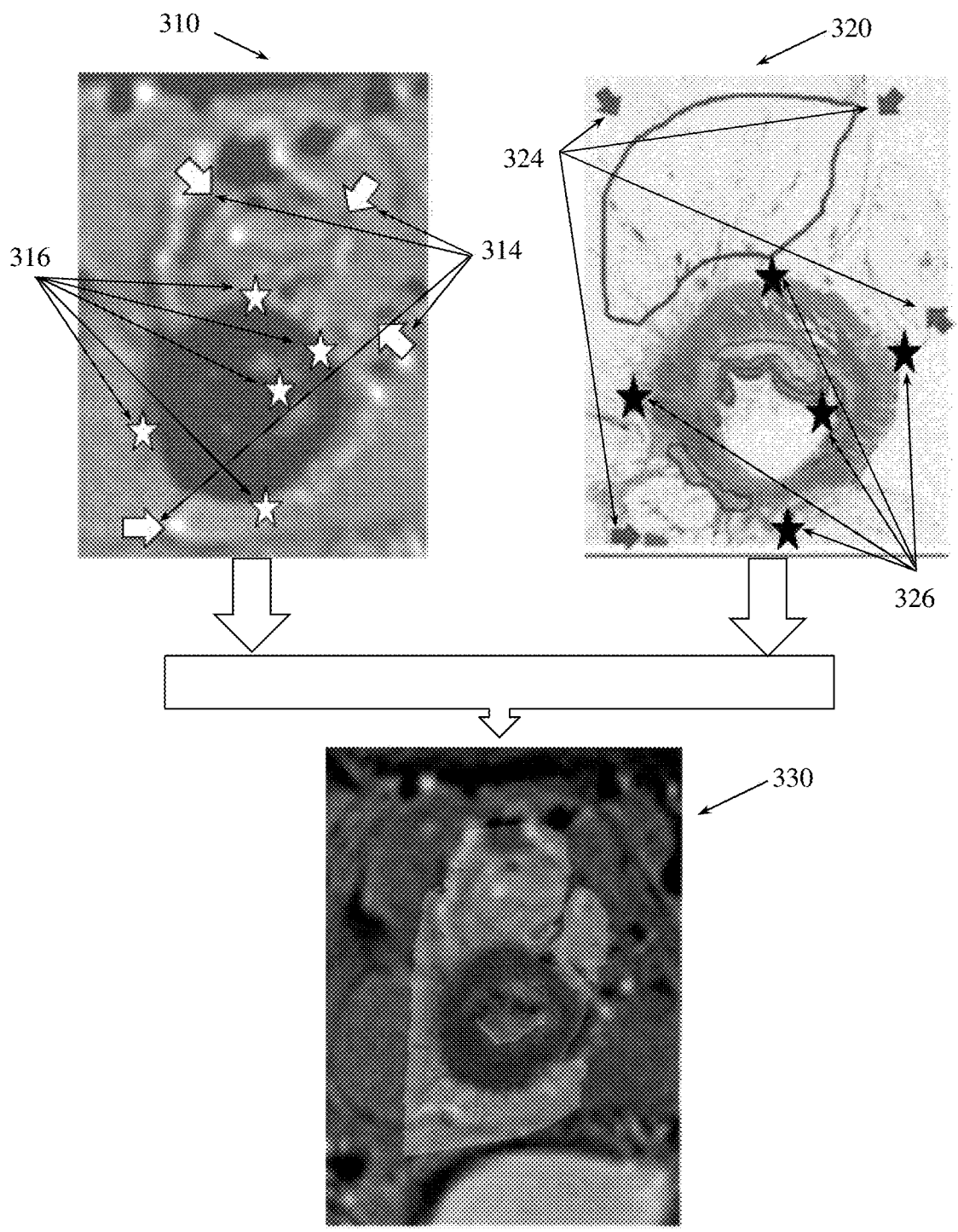
FIG. 3 illustrates a composite image generated from a pre-surgical MRI image registered with an annotated ex-vivo, post-surgical rectal pathology image.

FIG. 3 illustrates a registration approach used to generate composite image 330. Composite image 330 is generated by registering a pre-surgical MRI image 310 with an annotated ex-vivo, post-surgical rectal pathology image 320. The registration process illustrated in FIG. 3 presents one possible registration approach that is suitable for use by methods and apparatus described herein. Pre-surgical MRI image 310 includes anatomic structures 314 and anatomic structures 316. Anatomic structures 314 and anatomic structures 316 may be annotated by an expert pathologist, or may be annotated automatically. Annotated ex-vivo, post-surgical rectal pathology image 320 may be a whole-mount rectal pathology slice stained with H&E. Anatomic structures 324 and anatomic structures 326 may be annotated by an expert pathologist or may be annotated automatically. Anatomic structures 324, anatomic structures 326, anatomic structures 314, and anatomic structures 316 may indicate residual tumor structures, benign treatment effects of ulceration and fibrosis, or normal tissue, including mucosal layers or fat. Anatomic structures 324 and anatomic structures 326 correspond with anatomic structures 314 and anatomic structures 316. Example methods and apparatus may co-register anatomic structures 324 and anatomic structures 326 with anatomic structures 314 and anatomic structures 316 using non-linear alignment of pre-surgical MRI image 310 with post-surgical rectal pathology image 320. Example methods and apparatus may quantitatively fuse pathology data with radiology data by registering corresponding anatomic structures using thin-plate spline-based elastic registration to warp matched landmarks and gross anatomy represented in pre-surgical MRI image 310 and annotated ex-vivo, post-surgical rectal pathology image 320 into spatial alignment. Composite image 330 represents the spatially correlated pre-surgical MRI image 310 and annotated ex-vivo, post-surgical rectal pathology image 320. By generating composite image 330, example methods and apparatus improve the detection of integrated radiology/pathology information, which improves the prediction of treatment response and improves early patient outcomes when treating colorectal cancer. Example methods and apparatus improve the mapping of the pathological extent represented on MRI images for different treatment effects, including ulceration and fibrosis, as well as residual cancer. Example methods and apparatus may identify, in a member of the set of composite images, a texture feature or a shape feature associated with invasive cancerous pathology. In another embodiment, example methods and apparatus may generate a composite image by registering a pre-chemoradiation MRI image with a post-chemoradiation MRI image using affine co-registration and deformable co-registration.

In one example, a method may be implemented as computer executable instructions. Thus, in one example, a computer-readable storage device may store computer executable instructions that if executed by a machine (e.g., computer) cause the machine to perform methods described or claimed herein including method 100, method 200, and method 500. While executable instructions associated with the listed methods are described as being stored on a computer-readable storage device, it is to be appreciated that executable instructions associated with other example methods described or claimed herein may also be stored on a computer-readable storage device. In different embodiments, the example methods described herein may be triggered in different ways. In one embodiment, a method may be triggered manually by a user. In another example, a method may be triggered automatically.

Figure 4:
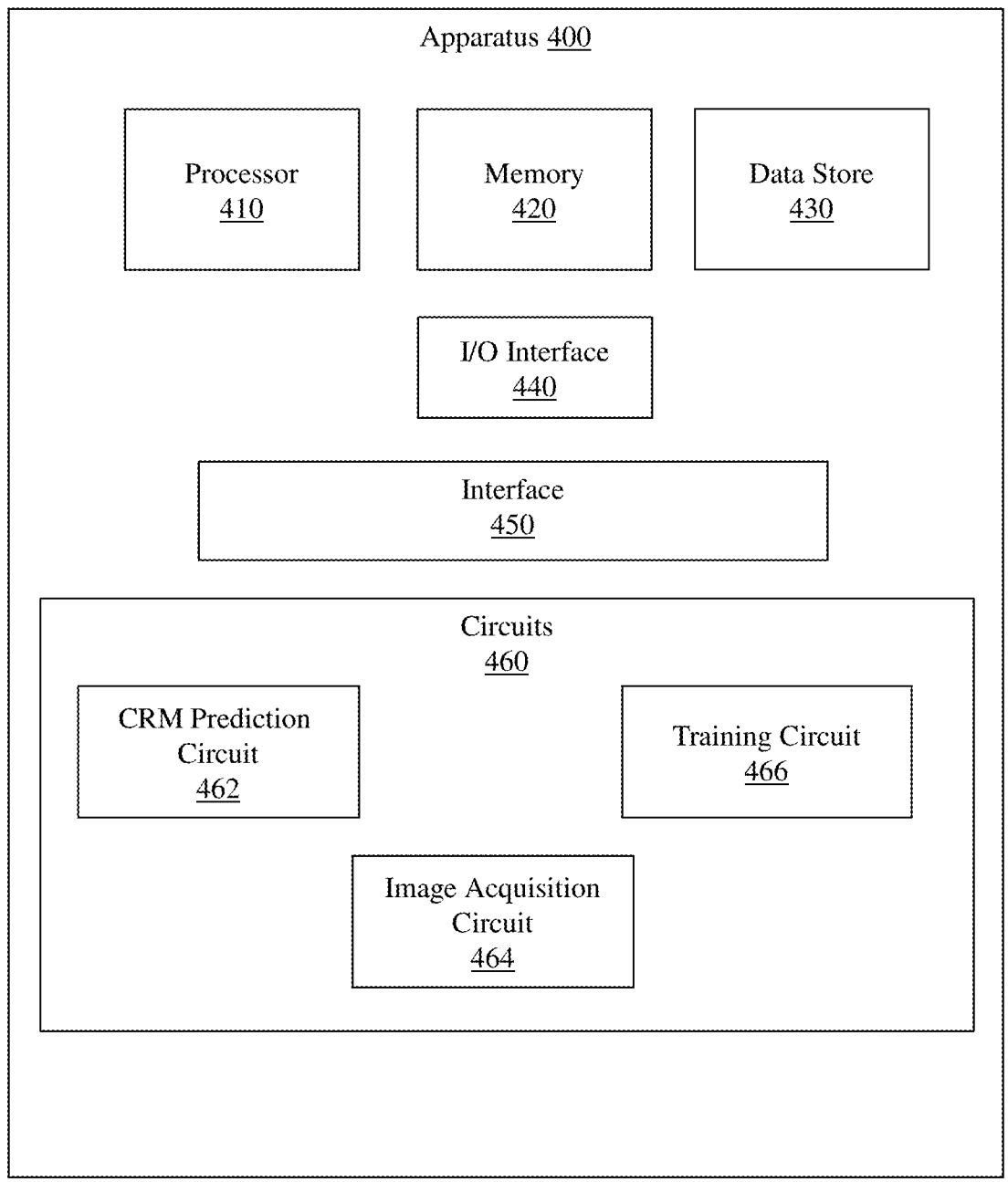
FIG. 4 illustrates an example apparatus for generating a CRM probability score.

FIG. 4 illustrates an example apparatus 400. Apparatus 400 may be used for generating a CRM probability score for a region of tissue represented in a diagnostic radiological image. Apparatus 400 may be used to generate a pre-operative surgical plan. In one embodiment, apparatus 400 distinguishes CRM positive tissue from CRM negative tissue in a region of tissue demonstrating cancerous pathology. Apparatus 400 includes a processor 410, a memory 420, a data store 430, an input/output (I/O) interface 440, a set of circuits 460, and an interface 450 that connects the processor 410, the memory 420, the data store 430, the I/O interface 440, and the set of circuits 460. Data store 430 stores a set of radiological images of tissue demonstrating cancerous pathology. In one embodiment, data store 430 stores a set of radiological images of tissue that is CRM positive or CRM negative. A member of the set of radiological images includes a texture feature, a shape feature, or other radiomic feature.

The set of circuits 460 includes a CRM prediction circuit 462, an image acquisition circuit 464, and a training circuit 466. In one embodiment, the functionality associated with the set of circuits 460 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 460 are implemented as ASICs or SOCs.

CRM prediction circuit 462 generates a CRM probability score. The CRM probability score is based, at least in part, on a diagnostic radiological image of a region of tissue demonstrating colorectal pathology. The CRM probability score indicates the probability that the region of tissue represented in the diagnostic radiological image is CRM positive. In one embodiment the CRM prediction circuit 462 generates the CRM probability score based on the diagnostic radiological image of the region of tissue and a texture feature or a shape feature extracted from the diagnostic radiological image.

Image acquisition circuit 464 accesses a diagnostic radiological image of a region of tissue demonstrating colorectal cancer pathology. The diagnostic radiological image includes a texture feature or a shape feature, or other radiomic feature. Image acquisition circuit 464 provides the diagnostic radiological image to CRM prediction circuit 462.

Training circuit 466 trains the CRM prediction circuit 462 using the set of radiological images. Training the CRM prediction circuit 462 increases the accuracy with which CRM prediction circuit 462 quantifies chemoradiation response in the region of tissue represented by the diagnostic radiological image. In one embodiment, training circuit 466 trains the CRM prediction circuit 462 using a set of texture features or shape features extracted from a set of post-neoadjuvant chemotherapy, pre-surgery MRI images of a region of tissue demonstrating colorectal cancer and an annotated copy of the set of post-neoadjuvant chemotherapy, pre-surgery MRI images. In another embodiment, training circuit 466 trains the CRM prediction circuit 462 using a set of composite images. Training circuit 466 generates the set of composite images by registering a member of the set of post-neoadjuvant chemotherapy, pre-surgery MRI images with a post-surgery whole-mount pathology slice of the region of tissue represented by the member of the set of post-neoadjuvant chemotherapy, pre-surgery MRI images. Training circuit 466 registers the pre-surgery MRI image with the post-surgery pathology slice using deformable co-registration. In one embodiment, training circuit 466 trains a support vector machine (SVM) using the set of composite images as a set of training examples.

In one embodiment, the set of circuits 460 also includes a display circuit. The display circuit controls a computer assisted diagnostic (CADx) system to display the CRM probability score, the diagnostic radiological image, the texture feature, the shape feature, or a member of the set of composite images. By displaying the diagnostic radiological image along with the probability score, the texture feature, the shape feature, or a member of the set of composite images, example apparatus provide a timely and intuitive way for a human pathologist to more accurately classify pathologies demonstrated by a patient, thus improving on conventional approaches to characterizing cancerous invasion, or predicting cancer recurrence and disease progression. Example apparatus also provides an improved way to generate pre-operative surgical plans.

Figure 5:
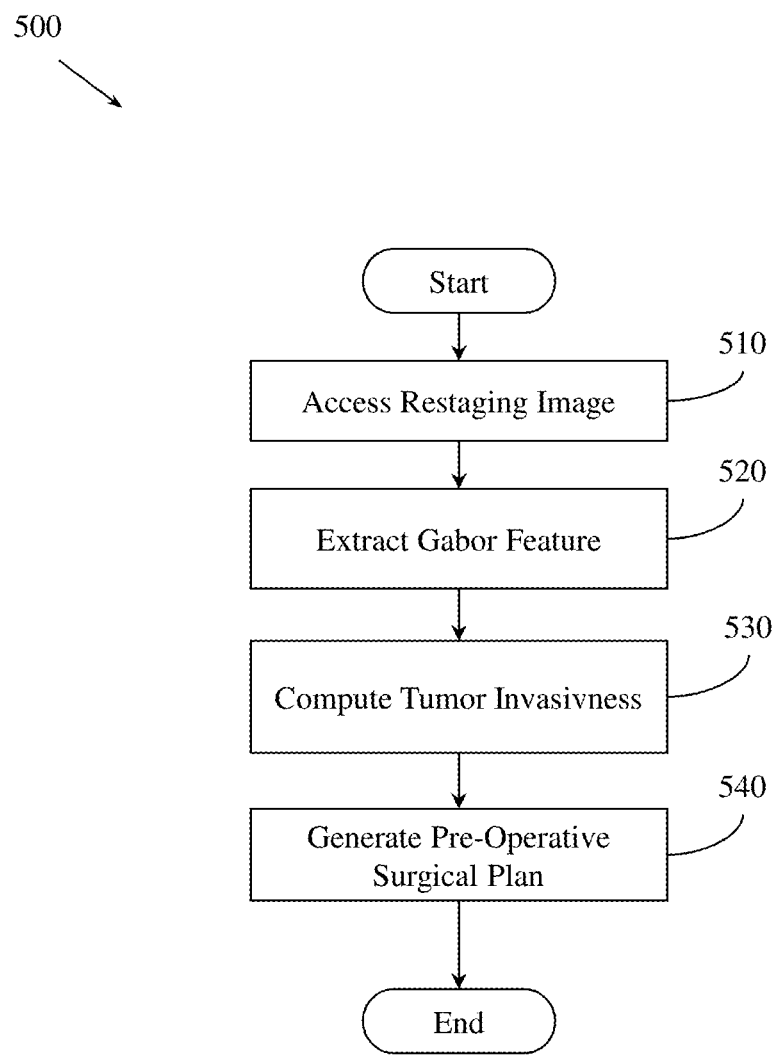
FIG. 5 illustrates an example method for pre-operative planning.

FIG. 5 illustrates an example method 500 for pre-operative planning. Method 500 includes, at 510, accessing a restaging radiological image of region of tissue demonstrating cancerous pathology. The restaging radiological image may be a 3T restaging T2w MRI image. In another embodiment, the restaging radiological image may be a different type of radiological image.

Method 500 also includes, at 520, extracting a Gabor radiomic feature map from the radiological image. The Gabor radiomic feature map captures structural homogeneity and structural heterogeneity characteristics of tissue represented in the radiological image. In one embodiment, other radiomic features, including other, different texture features or shape features may be extracted from the radiological image. The Gabor radiomic feature map may be extracted using, for example, a pattern analysis device using computer-vision approaches employing Gabor filters.

Method 500 also includes, at 530, computing a level of tumor invasiveness in the region of tissue. Method 500 may compute the level of tumor invasiveness based, at least in part, on the Gabor radiomic feature map. Computing the level of tumor invasiveness may include classifying the region of tissue as CRM positive or CRM negative.

Method 500 also includes, at 540, generating a pre-operative surgical plan based on the level of tumor invasiveness. The pre-operative surgical plan may, for example, identify a region of tissue to be treated by an automated ablation device or to be resected by a surgeon. By computing a level of tumor invasiveness based on the Gabor feature map, method 500 improves on conventional approaches by quantifying micro-architectural differences between different tissue regions, thereby facilitating more accurate characterization of tumor extent prior to surgery. Improved pre-operative surgical planning may reduce the number of patients exposed to unneeded and potentially dangerous surgical interventions and side effects.

Figure 6:
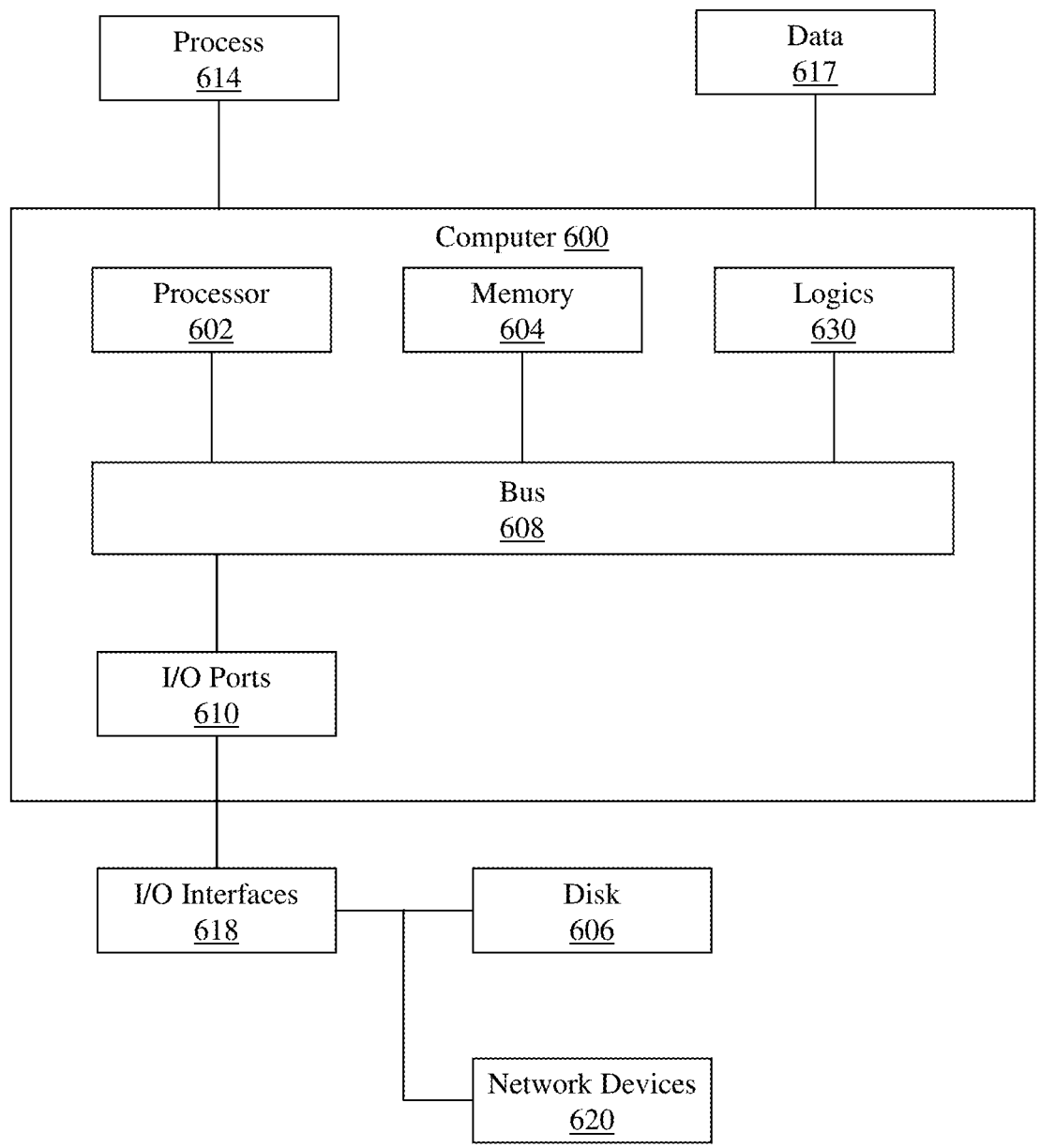
FIG. 6 illustrates an example computer in which example methods and apparatus described herein operate.

FIG. 6 illustrates an example computer 600 in which example methods illustrated herein can operate and in which example circuits may be implemented. In different examples, computer 600 may be part of an MRI system or a CT system, may be operably connectable to an MRI system or a CT system, or may be part of a CADx system.

Computer 600 includes a processor 602, a memory 604, and input/output ports 610 operably connected by a bus 608. In one example, computer 600 may include a set of circuits 630 that perform a method of predicting colorectal cancer tumor invasiveness. Thus, the set of circuits 630, whether implemented in computer 600 as hardware, firmware, and/or a combination thereof may provide means for predicting colorectal cancer tumor invasiveness. In different examples, the set of circuits 630 may be permanently and/or removably attached to computer 600. In one embodiment, the functionality associated with the set of circuits 630 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 630 are implemented as ASICs or SOCs.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, or a memory stick. Furthermore, disk 606 may include optical drives like a CD-ROM or a digital video ROM drive (DVD ROM). Memory 604 can store processes 614 or data 617, for example. Disk 606 or memory 604 can store an operating system that controls and allocates resources of computer 600.

Bus 608 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, digital whole slide scanners, an optical microscope, a keyboard, a microphone, a pointing and selection device, cameras, video cards, displays, disk 606, network devices 620, or other devices. Input/output ports 610 can include but are not limited to, serial ports, parallel ports, or USB ports.

Computer 600 may operate in a network environment and thus may be connected to network devices 620 via I/O interfaces 618 or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic device, an application specific integrated circuit (ASIC), a compact disk (CD), other optical device, a random access memory (RAM), a read only memory (ROM), a memory chip or card, a memory stick, and other media or device from which a computer, a processor or other electronic device can read.

"Circuit", as used herein, includes but is not limited to discrete hardware, (e.g., resistors, capacitors, transistors), integrated circuits, firmware, or combinations of each to perform a function(s) or an action(s), and/or to cause a function or action from another circuit, method, and/or system. A circuit may be a software controlled microprocessor, a discrete circuit (e.g., ASIC), an analog circuit, a digital circuit, a programmed logic device, a memory device containing instructions, and other entities. A circuit may include one or more gates, combinations of gates, or other circuit components. Where multiple circuits are described, it may be possible to incorporate the multiple circuits into one physical circuit. Similarly, where a single circuit is described, it may be possible to distribute that single circuit between multiple circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed control a processor configured to perform operations for predicting colorectal cancer tumor invasiveness, the operations comprising:
   accessing a magnetic resonance imaging (MRI) image of a region of tissue demonstrating colorectal cancer pathology;
   extracting a first set of radiomic features from the MRI image;
   providing the first set of radiomic features to an automated colorectal cancer classifier, wherein the automated colorectal cancer classifier comprises a support vector machine (SVM) configured to generate a classification of the region of tissue as circumferential resection margin (CRM) positive or CRM negative, based, at least in part, on the first set of radiomic features;

receiving, from the automated colorectal cancer classifier, the classification of the region of tissue as CRM positive or CRM negative;

generating a pre-operative surgical plan based, at least in part, on the classification; and displaying the classification and at least one of: the pre-operative surgical plan, the first set of radiomic features, or the MRI image.

2. The non-transitory computer-readable storage device of claim 1, the operations further comprising training the automated colorectal cancer classifier to distinguish CRM positive tissue from CRM negative tissue, where training the automated colorectal cancer classifier comprises:

accessing a set of MRI images of a region of tissue demonstrating colorectal cancer pathology;

extracting a second set of radiomic features from the set of MRI images;

generating an annotated set of MRI images from the set of MRI images;

generating a set of radiomic feature statistics from the second set of radiomic features;

obtaining a pre-treatment carcinoembryonic antigen (CEA) level for the region of tissue;

obtaining a post-treatment CEA level for the region of tissue;

computing a CEA ratio based on the pre-treatment CEA level and the post-treatment CEA level;

identifying a subset of radiomic features by correlating the set of radiomic feature statistics with the CEA ratio;

selecting an optimal combination of radiomic features from the subset of radiomic features; and updating the automated colorectal cancer classifier using the optimal combination of radiomic features and the annotated set of MRI images.

3. The non-transitory computer-readable storage device of claim 1, the operations further comprising training the automated colorectal cancer classifier using a set of composite images, where a member of the set of composite images is generated by registering a pre-surgical MRI image of a region of tissue demonstrating colorectal cancer with an annotated ex-vivo, post-surgical rectal pathology image of the region of tissue, or where a member of the set of composite images is generated by registering a pre-chemoradiation MRI image of a region of tissue demonstrating colorectal cancer with a post-chemoradiation MRI image of the region of tissue using affine co-registration and deformable co-registration.

4. The non-transitory computer-readable storage device of claim 3, where the pre-surgical MRI image is registered with the annotated ex-vivo, post-surgical rectal pathology image using thin-plate control-point spline based elastic registration.

5. The non-transitory computer-readable storage device of claim 4, where the annotated ex-vivo, post-surgical rectal pathology image is annotated for residual colorectal cancer, chemoradiation treatment effects, and normal tissue.

6. The non-transitory computer-readable storage device of claim 5, where chemoradiation treatment effects include fibrosis or mucosal ulceration.

7. The non-transitory computer-readable storage device of claim 1, wherein the MRI image is a 3 Tesla (T) T2 weighted (T2w) image.

8. The non-transitory computer-readable storage device of claim 1, where the first set of radiomic features comprises at least one of: a textural feature, a gray level feature, a gradient feature, a Haralick feature, a difference entropy statistic, or a multi-scale oriented Gabor feature map.

9. The non-transitory computer-readable storage device of claim 8, where the texture feature comprises a first order statistic.

10. The non-transitory computer-readable storage device of claim 9, where the first set of radiomic features are extracted from the MRI image on a per-voxel basis.

11. The non-transitory computer-readable storage device of claim 2, where selecting an optimal combination of radiomic features comprises performing a principal component analysis (PCA) or a logistic regression on the subset of radiomic features.

12. The non-transitory computer-readable storage device of claim 11, where the optimal combination comprises at least ten features.

13. The non-transitory computer-readable storage device of claim 12, where the optimal combination comprises at least one Gabor feature.

14. The non-transitory computer-readable storage device of claim 1, wherein the automated colorectal cancer classifier generates the classification of the region of tissue as CRM positive or CRM negative with at least a ninety percent accuracy rate.

15. The non-transitory computer-readable storage device of claim 1, the operations further comprising training the automated colorectal cancer classifier, or a second, different automated colorectal cancer classifier, to classify a response to a treatment demonstrated by a region of tissue, where training the automated colorectal cancer classifier or the second, different automated colorectal cancer classifier comprises:

accessing a set of MRI images of a region of tissue demonstrating colorectal cancer pathology;

extracting a third set of radiomic features from the set of MRI images;

generating an annotated set of MRI images from the set of MRI images;

generating a second set of radiomic feature statistics from the third set of radiomic features;

identifying a second subset of radiomic features by identifying a subset of the third set of radiomic features that identifies the response to the treatment demonstrated by the region of tissue;

selecting a second optimal combination of radiomic features from the second subset of radiomic features; and updating the automated colorectal cancer classifier or the second, different automated colorectal cancer classifier using the second optimal combination of radiomic features and the annotated set of MRI images.

16. The non-transitory computer-readable storage device of claim 15, where the response to the treatment includes a pathologic stage, a pathologic tumor regression grade, a pathologic tumor type, or a pathologic tumor differentiation level.

17. The non-transitory computer-readable storage device of claim 16, the operations further comprising:

computing a probability that the region of tissue will experience a five year local recurrence of colorectal cancer based, at least in part, on the first set of radiomic features and the classification; and generating a pre-operative surgical plan based, at least in part, on the probability that the region of tissue will experience a five year local recurrence.

* * * * *